US00PP08978P

United States Patent [19]

Friday

[11] Patent Number: Plant 8,978

[45] Date of Patent: Nov. 15, 1994

[54] P.F. 15A PEACH TREE

[76] Inventor: Paul J. Friday, P.O. Box 850, Coloma, Mich. 49038

[21] Appl. No.: 158,891

[22] Filed: Nov. 29, 1993

[51] Int. Cl.[5] ..... A01H 5/00
[52] U.S. Cl. ..... Plt./43.2
[58] Field of Search ..... Plt. 43.2

[56] References Cited

U.S. PATENT DOCUMENTS

P.P. 8,211 4/1993 Janzen .

*Primary Examiner*—James R. Feyrer
*Attorney, Agent, or Firm*—Fred P. Kostka

[57] ABSTRACT

A new and distinct variety of peach tree having the following unique combination of desirable features:

1. Producing a very firm fruit having a resilient flesh texture.
2. Blossoms are non-showy when in full bloom.
3. A substantially spheriodal fruit with yellow flesh having red mottling.
4. Early maturing fruit of good taste.
5. A mid-season peach variety which matures after Redhaven and which has good storage and shelf life.
6. A stone having an arcuate base.

1 Drawing Sheet

ORIGIN OF THE VARIETY

The new peach tree (hereinafter refrred to as the 'P.F. 15A' Peach Tree) was originated by Paul Friday in the experimental orchard, which is maintained for the purpose of breeding peach trees, at Paul Friday Farms Inc., located in Coloma, Mich. Coloma is located in the southwest portion of Michigan. In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimentl orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. 15A', was a selection from one such a seedling population, and was based on the numerous superior genetic attributes of this tree which are described in the botanical descriptions to follow.

ASEXUAL REPRODUCTION OF THE VARIETY

The new and distinct variety of peach tree was asexually propagated by budding as performed in the experimental orchard of Paul Friday Farms Inc. located in Coloma, Mich. The asexual propagation demonstrates that such reproduction of the charcteristics of the tree are consistent and are established and transmitted through succeeding propagation.

SUMMARY OF THE VARIETY

The new and distinct variety of peach tree is of moderate upright growth and a regular and productive bearer of peaches. The blossoms are characterized by being contracted or partially spread when in full bloom.

The blossoms of the present peach tree at full bloom may be characterized as being non-showy; i.e., angularly spaced five blossom petals projecting upwardly at an inclined angle so as to form a blossom, having a diameter of about ¾" measured across the blossoms. The typical non-showy blossom as exemplified for example by the Redhaven peach has five (5) radially extending and angularly spaced petals projecting upwardly at a relatively steep inclined angle so that the diametrical measurement across the outer edges of the petals is about ½".

The flesh of the fruit of the present peach tree is firm and is yellow with some red mottling in the flesh.

The skin is smooth and is of dark red color over about eighty (80%) percent of its surface at maturity. The red color occurs over about sixty (60%) of the surface about 10 days prior to maturity. At maturity the peach is substantially spheroidal but with a pronounced suture with the diameter ranging between about 2½" to 3 inches.

It is noteworthy that the fruit of this tree is further characterized as having smooth, gently rounded cheeks at the blossom end of the fruit. These protrude to form fruit surfaces higher than the blossom point. This characteristic reduces fruit damage in harvest, shipping and storage, by reducing the exposure of and damage to the apical blossom protrusion in handling. Thus breaching of the skin and formation of an entry point for microorganisms which cause rot in many other commercially important peach varieties harvested in the same production period is avoided in this fruit.

The fruit has a firm flesh and may be described as resilient to the extent that the flesh is yieldable and restorable to its original state when subjected to impact forces which may cause permanent deformities in peached of the commercial varieties. The firmness of the fruit facilitates handling and packaging of the peaches without damaging the same for shipment. This results in less spoilage and also increases the shelf life.

The fruit matures in the middle part of the peach growing seasons of Southwestern Michigan. The fruit as mentioned heretofore is of red color over about eighty (80%) percent of its spheroidal surface and has a very attractive appearance.

BRIEF DESCRIPTION OF THE PHOTOGRAPHS

The accompanying photographs of the new variety show:

In the top photograph, typical fruit of the treee attached to a stem with leaves remaining, a detached fruit showing the color and character of the stem end of the fruit, and a detached fruit split along the suture plane to show the color and character of the fruit flesh, the pit cavity, and a detached pit;

A middle photograph shows the terminal portion of a typical stem of the variety in blooming season, with flowers shown in varying stages of opening and their pink color. This photograph also shows the growth of new foliage during the flowering period and bark of the previous growing season is also shown to be of brown color and lacking conspicuous lenticels; and, The bottom photograph shows the interior of the canopy of the tree to be of light to moderate density, and also shows the color of mature bark and the strong angles of scaffold branches. This photograph also shows the uniform placement of fruit about the specimen depicted, which has been pruned to have an open center.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Panatone Matching System (PMS) as used internationally to identify printed colors.

Tree:
- *Height.*—Unpruned 17'.
- *Width.*—Unpruned 12'.
- *Size.*—Medium-large.
- Vigor.—Medium vigor terminal growth of 1' to 4' per year.
- *Density.*—Medium, pruning requirements heavy.
- *Form.*—Upright. Branches extend at crotch angles of about 90 degrees.
- *Production.*—Productive, approximately ½ of the fruit annually must be removed.
- *Bearer.*—Consistent.
- *Disease resistance to bacterial leaf and fruit spot.*—Very good.

Trunk:
- *Bark.*—Grayish brown (4635u).
- *Size.*—Medium.
- *Surface.*—Medium shaggy.

Branches:
- *Size.*—Medium.
- *Surface.*—Medium.
- *Lenticels.*—Medium number and length 2/16" to 5/16".
- *Color.*—Brown (470c).

Leaves:
- *Size.*—Large. Average length — 6½" to 7". Average width — 1¾".
- *Form.*—Lanceolate — pointed.
- *Thickness.* —Medium.
- *Texture.*—Medium.
- *Margin.*—Serrate.
- *Petiole.*—Medium length — medium thickness.
- *Gland.*—Varies from 1 to 5, usually 2 — one on either side of base of leaf or upper portion of petiole.
- *Gland color.*—Yellow.
- *Color.*—Upper surface: green (350c). Surface: dull green (349c).

Flower buds:
- *Size.*—Medium.
- *Length.*—Medium.

Flowers:
- *Blooming period.*—Mid-season, May 5, 1993 to May 7, 1993.
- *Size.*—Medium or partially showy petal pattern (about ¾" diameter).
- *Pollen.*—Present, self-fertilizing.
- *Color.*—At bloom, half open — pink (190u); before petal fall, reddish pink (707c).

Fruit:
- *Maturity when described.*—Firm ripe.
- *Date of first picking.*—Aug. 17, 1993 (About 9 days after picking Redhaven — Aug. 8, 1993. Fruit matures very evenly and can be picked in 1 or 2 pickings.)
- *Date of last picking.*—Also Aug. 17, 1993.
- *Size.*—Large sphere. Average diameter — 2-⅝".
- *Form.*—Oblate spherical.
- *Suture.*—Somewhat pronounced.

Skin:
- *Thickness.*—Medium.
- *Texture.*—Tough, tenacious to skin.
- *Tendency to crack.*—None.
- *Down.*—Moderate to little
- *Color.*—Yellow ground color (134c). Nearly overspread (80%) with red (174c) to (173c).

Flesh:
- *Texture.*—Firm, similar to a cling peach relatively free of fiber, non-melting.
- *Ripens.*—On suture first.
- *Flavor.*—Good.
- *Aroma.*—Pleasant.
- *Eating quality.*—Good.
- *Color.*—Yellow (106u). Pit cavity red (198a) with some red mottled through the flesh (190u).

Stone:
- *Type.*—Freestone.
- *Size.*—Average length — 1½". Average width — 1". Average thickness — ⅝".
- *Form.*—Arcuate.
- *Base.*—Straight.
- *Apex.*—Arcuate.
- *Sides.*—Nearly equal.
- *Surface.*—Irregularly furrowed.
- *Color.*—Reddish brown (201u).
- *Tendency to crack.*—None.

Use: Desert:
Shipping quality: Good.
Keeping quality: Excellent.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as illustrated and described as large size, vigorous and upright in growth and a regular and productive bearer of medium large size, yellow flesh with some red mottling, freestone fruit with good flavor and eating quality; and being further characterized by a partially showy blossom about ¾" diameter when in full bloom, said fruit at maturity being of substantially spheroidal shape with firm flesh and a red skin color covering 80% of the fruit and having a moderately pronounced suture, said maturity occurring about 9 days after maturity of the Redhaven peach.

* * * * *

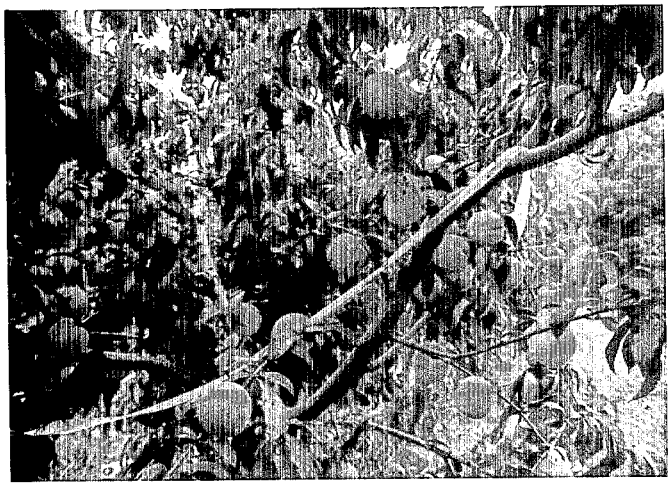

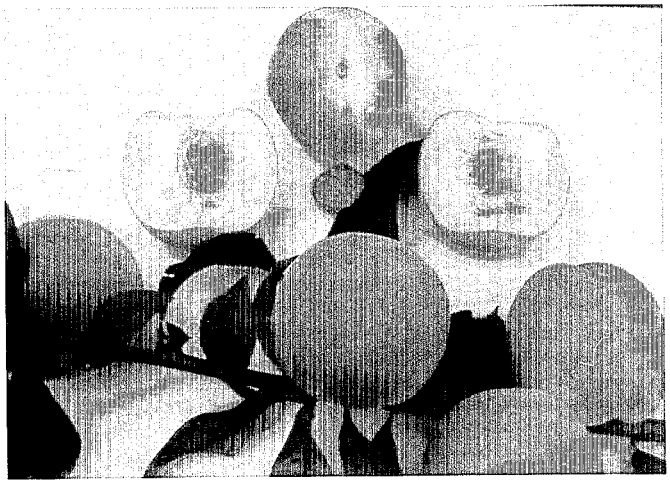
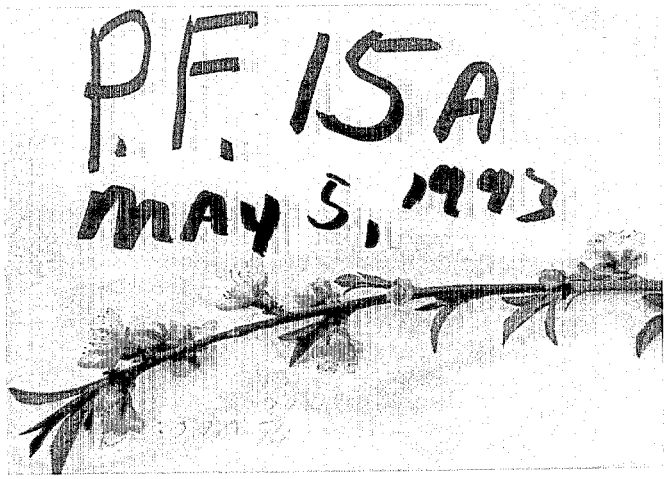
P.F. 15A
MAY 5, 1993